United States Patent [19]

Hara et al.

[11] Patent Number: 5,248,827
[45] Date of Patent: Sep. 28, 1993

[54] PROCESS FOR PRODUCING AN ETHYLENAMINE

[75] Inventors: Yasushi Hara, Shinnanyo; Toshio Hironaka, Tokuyama; Noritaka Nagasaki, Shinnanyo; Nobuyuki Kanai, Kudamatsu; Nobumasa Suzuki, Shinnanyo; Yukio Ito, Kudamatsu; Takanori Miyake, Yokkaichi, all of Japan

[73] Assignee: Tosoh Corporation, Shinnanyo, Japan

[21] Appl. No.: 761,003

[22] Filed: Sep. 17, 1991

[30] Foreign Application Priority Data

| Sep. 17, 1990 | [JP] | Japan | 2-243830 |
| Nov. 28, 1990 | [JP] | Japan | 2-322352 |
| Dec. 27, 1990 | [JP] | Japan | 2-415070 |
| Jun. 4, 1991 | [JP] | Japan | 3-159435 |
| Jun. 4, 1991 | [JP] | Japan | 3-159437 |
| Jul. 4, 1991 | [JP] | Japan | 3-189572 |

[51] Int. Cl.$^5$ .............................. C07C 209/16
[52] U.S. Cl. ...................... 564/480; 546/184; 546/246; 564/511; 564/512
[58] Field of Search ............ 564/480, 511, 512; 546/184, 246

[56] References Cited

U.S. PATENT DOCUMENTS

| 4,760,190 | 7/1988 | Twigg | 564/480 |
| 4,827,037 | 5/1989 | Doumaux, Jr. | 564/479 |

FOREIGN PATENT DOCUMENTS

| 0069322 | 1/1983 | European Pat. Off. . |
| 0197611 | 10/1986 | European Pat. Off. . |
| 0211552 | 2/1987 | European Pat. Off. . |
| 0315189 | 5/1989 | European Pat. Off. . |

*Primary Examiner*—Richard L. Raymond
*Assistant Examiner*—Scott C. Rand
*Attorney, Agent, or Firm*—Oblon, Spivak, McClelland, Maier & Neustadt

[57] ABSTRACT

A process for producing an ethylenamine, which comprises reacting ammonia and/or an ethylenamine with an ethanolamine in the presence of hydrogen to obtain an ethylenamine having an increased number of ethylene chains over the ammonia and/or the ethyelenamine used as the starting material, wherein a catalyst comprising Ni and M elements wherein M is at least one rare earth element selected from the group consisting of scandium, yttrium, praseodymium, neodymium, samarium, europium, gadolinium, terbium, dysprosium, holmium, erbium, thulium, ytterbium and lutetium, is used for the reaction.

10 Claims, No Drawings

PROCESS FOR PRODUCING AN ETHYLENAMINE

The present invention relates to a process for producing an ethylenamine. More particularly, it relates to a process for producing an ethylenamine, which is characterized by the use of a catalyst comprising Ni and M elements, wherein M is at least one rare earth element selected from the group consisting of scandium, yttrium, praseodymium, neodymium, samarium, europium, gadolinium, terbium, dysprosium, holmium, erbium, thulium, ytterbium and lutetium. Ethylenamines are aliphatic amine compounds useful for e.g. agricultural chemicals, chelating agents, epoxy-curing agents, wet paper strength-increasing agents or additives for lubricant oils.

As a conventional process for producing ethylenamines, a process is known wherein ethylene dichloride is used as a starting material and is reacted with ammonia. This process is widely used, and it is thereby possible to produce an ethylenamine of industrially useful quality containing no substantial cyclic products. However, this process has a problem that a large amount of sodium chloride is formed as by-product, and its separation and treatment are costly. As a process which is free from the problem of by-product, a process is widely employed wherein a monoethanolamine is used as a starting material and is reacted with ammonia in the presence of hydrogen. This process is characterized by the use of a catalyst, and various catalysts have been proposed.

Conventional catalysts include, for example, Ni+Cu+Cr (U.S. Pat. No. 3,151,115), Ni+Fe (U.S. Pat. No. 3,766184), Ni+Cu (Japanese Unexamined Patent Publication No. 88892/1979), Ni+Co+Cu (U.S. Pat. No. 4,014,933) and Ni+Re (Japanese Unexamined Patent Publication No. 108534/1981). All of these catalysts contain Ni and have second and third components incorporated to improve the performance of the catalysts. However, with these catalysts, cyclic products such as piperazine and amines containing hydroxyl groups will be formed in substantial amounts. Thus, they are not satisfactory from the viewpoint of selectivity. Further, they are not industrially satisfactory also from the viewpoint of the catalytic activities.

As described above, many catalysts have been disclosed for a process for producing ethylenamines using monoethanolamine free from the problem of by-product. However, such catalysts have low activities and can not be regarded as industrially satisfactory catalysts, since cyclic products and hydroxyl group-containing amines are produced in substantial amounts as by-products.

Thus, it has been desired to develop a process for producing an ethylenamine using a high performance catalyst having the catalytic activity and selectivity substantially improved over the conventional Ni-type catalysts.

Under these circumstances, the present inventors have conducted extensive studies on processes for producing ethylenamines and as a result, have found a new fact that when at least one member selected from the group consisting of scandium, yttrium, praseodymium, neodymium, samarium, europium, gadolinium, terbium, dysprosium, holmium, erbium, thulium, ytterbium and lutetium, is added to nickel, the catalyst will show very high catalytic activity and selectivity as compared with a case where such a member is not added. The present invention has been accomplished on the basis of this discovery.

Thus, the present invention provides a process for producing an ethylenamine, which comprises reacting ammonia and/or an ethylenamine with an ethanolamine in the presence of hydrogen to obtain an ethylenamine having an increased number of ethylene chains over the ammonia and/or the ethyelenamine used as the starting material, wherein a catalyst comprising Ni and M elements wherein M is at least one rare earth element selected from the group consisting of scandium, yttrium, praseodymium, neodymium, samarium, europium, gadolinium, terbium, dysprosium, holmium, erbium, thulium, ytterbium and lutetium, is used for the reaction.

Now, the present invention will be described in detail with reference to the preferred embodiments.

The catalyst to be used in the process of the present invention comprises Ni and M elements, wherein M is at least one rare earth element selected from the group consisting of scandium, yttrium, praseodymium, neodymium, samarium, europium, gadolinium, terbium, dysprosium, holmium, erbium, thulium, ytterbium and lutetium.

In the process of the present invention, Ni means a compound containing a nickel element or a single substance of nickel element, and M means a compound containing an element selected from the group consisting of scandium, yttrium, praseodymium, neodymium, samarium, europium, gadolinium, terbium, dysprosium, holmium, erbium, thulium, ytterbium and lutetium or a single substance of such element.

For example, Ni includes nickel metal, nickel oxide, nickel hydroxide, a nickel salt, a nickel alkoxide and a nickel complex. Among them, nickel metal and nickel oxide are preferred which are stable under the reaction conditions.

M includes a metal, an oxide, a hydroxide, a salt, an alkoxide and a complex. Specifically, it includes, for example, scandium oxide, yttrium metal, yttrium oxide, yttrium hydroxide, an yttrium salt such as yttrium nitrate, yttrium sulfate, yttrium fluoride, yttrium chloride or yttrium iodide, praseodymium oxide, a praseodymium salt, neodymium oxide, samarium oxide, samarium hydroxide, a samarium alkoxide, a samarium salt such as samarium nitrate, samarium sulfate, samarium chloride, samarium fluoride or samarium iodide, europium oxide, an europium salt, gadolinium oxide, gadolinium hydroxide, gadolinium metal, a gadolinium salt, a gadolinium alkoxide, terbium metal, terbium oxide, dysprosium oxide, dysprosium metal, dysprosium hydroxide, a dysprosium salt, a dysprosium alkoxide, holmium oxide, erbium metal, erbium oxide, thulium oxide, ytterbium metal, ytterbium oxide, ytterbium hydroxide, an ytterbium salt such as ytterbium nitrate, ytterbium sulfate, ytterbium chloride, ytterbium fluoride or ytterbium iodide, an ytterbium alkoxide, lutetium metal, lutetium oxide, lutetium hydroxide, a lutetium salt, and a lutetium alkoxide. Among them, metals and oxides are preferred which are stable under the reaction conditions.

In the process of the present invention, Ni and M are used usually as supported on a carrier to improve the catalytic activity. However, they may not necessarily be supported on a carrier. When supported on a carrier, there may be employed as the carrier a metal oxide such as silica, alumina, titania, zirconia, magnesia, calcia, thoria, niobium oxide, zinc oxide or an oxide of a rare earth metal, a M oxide such as silica-calcia, silica-magnesia, silica-alumina, zeolite, pumice, diatomaceous earth or acid clay, silicon carbide, porous glass or active carbon. Some carriers have an interaction with Ni and M. Those having a strong interaction may have a chemical bond between the carriers and Ni or M, whereby the activities, selectivity, heat resistance or catalyst life may change. When Ni and M are to be supported on a carrier, they may simultaneously be supported, or they may separately be supported. There is no particular restriction as to the supporting method. The following methods may be mentioned, for example:

1) a method which is usually called an impregnation method, wherein solution of Ni and M is impregnated to a carrier.

2) a method which is usually called a coprecipitation method, wherein a solution of Ni and M and a solution having the carrier components dissolved therein are mixed, and a precipitation agent is added thereto for decomposition.

3) a method which is usually called a precipitation method, wherein a carrier is immersed in a solution of Ni and M, and then adding a precipitation agent under stirring to precipitate Ni and M on the carrier.

4) a method which is usually called a kneading method, wherein a precipitation agent is added to a solution of Ni and M to form precipitates, then a powder of carrier, hydrogel or hydrosol is added thereto, and the mixture is kneaded.

However, the catalyst may be supported on a carrier by any other method. A solution of Ni and M may be prepared by dissolving soluble salts or complexes of Ni and M in a solvent. For example, as a soluble salt or complex of Ni, nickel nitrate, nickel sulfate, nickel chloride, nickel bromide, nickel iodide, nickel acetate, nickel formate, nickel oxalate, a nickel alkoxide, nickel acetylacetonate or nickel carbonyl may be employed. As a soluble salt or complex of M, a nitrate, a sulfate, a chloride, an acetate, a carbonate, a fluoride, an iodide or an alkoxide of scandium, yttrium, praseodymium, neodymium, samarium, europium, gadolinium, terbium, dysprosium, holmium, erbium, thulium, ytterbium or lutetium, may be employed. After supported on a carrier, Ni and M may be converted to their oxides by hydrolysis and/or calcination, and they may further be converted to oxides or metals by reduction.

In the process of the present invention, it is not necessarily required to conduct calcination in air of a catalyst precursor for the preparation of the catalyst. It is difficult to define the conditions for the calcination and reduction, since they vary to large extents depending upon the types of Ni and M, the types of the carrier and the supporting method. However, if an example is given with respect to a case wherein nickel nitrate is used as Ni and yttrium nitrate, samarium nitrate or ytterbium nitrate is used as M, the temperature for calcination is at most 600° C. If the calcination temperature exceeds 600° C., the resulting nickel oxide tends to be sintered, whereby the catalytic activity tends to deteriorate. Further, when the obtained mixture comprising nickel oxide and yttrium oxide, samarium oxide or ytterbium oxide, is to be reduced, the reduction is conducted usually within a temperature range of from 100° to 650° C., preferably from 150° to 600° C., for from 30 minutes to a few days in the presence of hydrogen. If the temperature is lower than 100° C., reduction of nickel oxide tends to be inadequate, whereby the catalytic activity will be low. On the other hand, if the temperature is higher than 650° C., nickel tends to be sintered, whereby the catalytic activity tends to be low.

In a case where a nitrate of scandium, praseodymium, neodymium, europium, gadolinium, terbium, dysprosium, holmium, erbium, thulium or lutetium is used as M, the calcination temperature is preferably from 200° to 700° C. If the temperature is less than 200° C., the decomposition rates of nitrates of Ni and M tend to be low. On the other hand, if the calcination exceeds 700° C., oxides of Ni and M tend to be sintered, whereby the catalytic activity tends to be low, and nickel tends to be an aluminate, whereby the reducibility tends to deteriorate. As the atmospheric gas for calcination, air or nitrogen may be employed. If an example for the reduction conditions is given with respect to a case where activated alumina is used as a carrier and reduction is conducted with hydrogen gas, the temperature is preferably from 300° to 650° C. If the temperature is less than 300° C., the reduction rate of nickel tends to be low. On the other hand, if the temperature exceeds 600° C., Ni and M tend to be sintered, whereby the catalytic activity tends to deteriorate. However, when a carrier having a weaker interaction with Ni and M than activated alumina, such as silica, α-alumina, diatomaceous earth or glass is employed, nickel may adequately be reduced to nickel metal even at a low temperature at a level of not higher than 200° C.

In the process of the present invention, if the ratio of Ni to M is represented by an atomic ratio, when M is yttrium, samarium or ytterbium, the atomic ratio of Ni/M is preferably from 1 to 80, more preferably from 2 to 50. If the atomic ratio is less than 1 or more than 80, the catalytic activity and selectivity tend to be low.

When M is scandium, praseodymium, neodymium, europium, gadolinium, terbium, dysprosium, holmium, terbium, thulium or lutetium, the atomic ratio of Ni/M is preferably from 0.01 to 100, more preferably from 0.05 to 50. If the atomic ratio is less than 0.01 or more than 100, the catalytic activity and selectivity tend to be low.

The catalyst to be used in the process of the present invention may be in a powder form or may be molded into a granular, spherical, columnar, cylindrical or pellet form or in a non-specified form. The molding of the catalyst can be conducted by various methods such as a method wherein Ni and M are supported on a molded carrier, or a method wherein powdery Ni and M, or powdery carrier having Ni and M supported thereon, is molded by various methods such as tablet molding, extrusion molding, spray drying or rolling granulation. In a case of a suspended bed system, a powdery or granular catalyst may be employed, and in a case of a fixed bed system, a pellet-form, tablet-form, spherical or granular catalyst may be employed. When the catalyst is to be molded, a binder such as alumina sol, silica sol, titania sol, acid clay or clay may be incorporated.

In the process of the present invention, the catalyst may be used in an amount sufficient to let the reaction proceed at an industrially useful rate. The amount can not generally be defined, since it varies depending upon whether the reaction system is a suspended bed system or a fixed bed system. In the case of a suspended bed system, it is usual to use the catalyst in an amount of from 0.1 to 20% by weight relative to the total weight of the starting materials. If the amount is less than 0.1% by weight, no adequate reaction rate is obtainable, and if it exceeds 20% by weight, no further significant improvement in the catalytic activity tends to be obtained.

The starting materials to be used in the process of the present invention are an ethanolamine and ammonia and/or an ethylenamine.

In the process of the present invention, the ethanolamine is a compound with a molecule having an ethylene chain and having a hydroxyl group and an amino group in the molecule, and it may be, for example, monoethanolamine, diethanolamine, triethanolamine, N-(2-aminoethyl)ethanolamine, or N-(2-hydroxyethyl)piperazine. The ethylenamine is a compound having amino groups at both terminals of an ethylene chain, and it may be, for example, ethylenediamine, diethylenetriamine, triethylenetetramine, tetraethylenepentamine, pentaethylenehexamine, piperazine, N-(2-aminoethyl)piperazine or triethylenediamine. Ammonia may be used in a state free from water or in a form of aqueous ammonia.

The combinations of the starting materials to be used in the process of the present invention include:
(1) ammonia and an ethanolamine,
(2) an ethylenamine and an ethanolamine, and
(3) ammonia, an ethylenamine and an ethanolamine.

The reactions in the process of the present invention are sequential reactions, whereby a resulting amine serves as a starting material for the subsequent reaction. When monoethanolamine is used as the ethanolamine and ethylenediamine which is the lowest ethylenamine, is used as the starting material, ethylenediamine will be formed in the case of the combination (1) of the starting materials. The resulting ethylenediamine will further react to form diethylenetriamine, triethylenetetramine, piperazine and N-(2-aminoethyl)piperazine. In the combination (2) diethylenetriamine, triethylenetetramine, tetraethylenepentamine, piperazine and N-(2-aminoethyl)piperazine will be formed. Likewise, in the combination (3), ethylenediamine, diethylenetriamine, triethylenetetramine, piperazine and N-(2)-aminoethyl)piperazine will be formed. Namely, an ethylenamine having the number of ethylene chains increased over the ammonia and/or the ethylenamine used as starting material, will be formed. Further, ethanolamines having the number of ethylene chains increased will also be formed as by-products, but these ethanolamines will also be consumed by the sequential reactions.

With respect to the ratio of the starting materials to be used in the process of the present invention, the molar ratio of the ethylenamine/the ethanolamine is preferably from 0.1 to 20, more preferably from 0.5 to 10, and the molar ratio of the ammonia/the ethanolamine is preferably from 1 to 50, more preferably from 3 to 40 and most preferably from 5 to 30. If the ethanolamine is too small as compared with the ammonia and the ethylenamine, the reaction pressure will be too high to be practical. On the other hand, if the ethanolamine is too large as compared with the ammonia and the ethylenamine, cyclic amines which are industrially undesirable, such as piperazine, and ethanolamines other than the ethylenamine will be formed substantially as by-products.

In the process of the present invention, the reaction is conducted in the presence of hydrogen. The hydrogen is supplied in a molar ratio of the hydrogen/the ethanolamine of from 0.01 to 5, preferably from 0.02 to 4, more preferably from 0.04 to 3. If the molar ratio is smaller or larger than the above range, the reaction rate tends to be low.

In the process of the present invention, the reaction is conducted usually at a temperature of from 110° to 290° C., preferably from 140° to 260° C. If the temperature is lower than 110° C., the reaction rate tends to be substantially low, and if it exceeds 290° C., the pressure tends to be high and the decomposition of the amine occurs, such being not practical.

In the process of the present invention, the reaction may be conducted in a liquid phase or in a gas phase. However, in order to produce an ethylenamine of high quality, it is better to conduct the reaction in a liquid phase.

In the process of the present invention, the pressure can not generally be defined, since it varies substantially depending upon the starting materials, the reaction temperature, etc. However, the pressure may be at a level whereby the ethanolamine and the ethylenamine can be maintained in a liquid phase.

In the process of the present invention, a solvent may be employed. As such a solvent, the one capable of dissolving the ethylenamine and ammonia is preferred. For example, water, dioxane, diethylene glycol dimethyl ether or triethylene glycol dimethyl ether may be mentioned. However, other solvents may be employed.

In the process of the present invention, there is no particular restriction as to the reaction method. The reaction may be conducted by a batch method, a semi-batch method or a continuous method by a fixed bed system, a fluidized bed system or a mobile bed system.

In the method of the present invention, it is usual that after separating the catalyst from the reaction solution, unreacted starting materials are separated and recovered by distillation. The formed ethylenamines are also separated into the respective components by distillation. The distillation may be conducted in a batch system or in a continuous system.

In the process of the present invention, the starting materials and the formed ethylenamines may be recycled to the reaction zone, as the case requires. By recycling the formed ethylenamines to the reaction zone, it is possible to change the composition of ethylenamine products.

The present invention provides a process for producing an ethylenamine from an ethanolamine, wherein a catalyst comprising Ni and M elements having high catalytic activity and high selectivity, is used and thus is very useful from the industrial viewpoint.

Now, the present invention will be described in detail with reference to Examples. However, it should be understood that the present invention is by no means restricted to such specific Examples.

For the sake of convenience, ethylenamines and ethanolamines will be represented by the following abbreviations.

EDA: ethylenediamine
DETA: diethylenetriamine
TETA: triethylenetetramine
TEPA: tetraethylenepentamine
PIP: piperazine
AEP: N-(2-aminoethyl)piperazine
HEP: N-(2-hydroxyethyl)piperazine
MEA: monoethanolamine
AEEA: N-(2-aminoethyl)ethanolamine Further, the selectivity will be represented by the following formula.

$$\text{Selectivity (\%)} = \frac{\text{moles of the product} \times \text{number of ethylene chains in the product}}{\text{mols of consumed MEA} \times 100}$$

EXAMPLE 1

5.95 g of nickel nitrate hexahydrate and 0.51 g of yttrium nitrate hexahydrate were dissolved in 17.1 ml of water, and 4.56 g of silica gel powder was added thereto. The mixture was left to stand at room temperature. One hour later, water was distilled off under reduced pressure, and the obtained powder was dried at 120° C. for 16 hours. The dried powder was calcined under an air stream of 200 ml/min at 180° C. for one hour and further at 400° C. for one hour. After calcination, the powder was reduced with 30 ml/min of hydrogen under a nitrogen gas stream of 30 ml/min at 400° C. for two hours. At the time of calcination and reduction, the temperature raising rate was adjusted to a level of 10° C./min. The catalyst thereby obtained was designated as Catalyst A. The theoretical supported amounts of Catalyst A were 20% by weight of nickel and 2% by weight of yttrium based on the total weight of the catalyst, on an assumption that both nickel and yttrium were reduced to the metallic states. Into a 200 ml stainless steel autoclave equipped with an electromagnetic stirrer, 18 g of MEA, 50 g of ammonia and 1 g of Catalyst A were charged, and hydrogen was introduced at room temperature so that the hydrogen partial pressure became 20 kg/cm$^2$. Then, the temperature was raised to 200° C., and the reaction pressure reached 192 kg/cm$^2$ G. After the temperature rise, the reaction was conducted for three hours at the same temperature. After completion of the reaction, ammonia was recovered, and the reaction solution was analyzed by gas chromatography. The results are shown in Table 1.

EXAMPLE 2

A catalyst was prepared in the same manner as for Catalyst A except that 1.03 g of yttrium nitrate hexahydrate was employed. The obtained catalyst was designated as Catalyst B. The theoretical supported amounts of Catalyst B were 20% by weight of nickel and 4% by weight of yttrium based on the total weight of the catalyst, on an assumption that both nickel and yttrium were reduced to the metallic states.

As a result of measurement of X-ray diffraction of the catalyst, only the diffraction peak of nickel was ascertained, and the crystal size of nickel was 12.6 nm as obtained from the Scherrer's formula.

The reaction was conducted in the same manner as in Example 1 except that 1 g of Catalyst B was used as the catalyst. After the temperature rise, the reaction pressure reached 193 kg/cm$^2$ G. The results of the reaction are shown in Table 1.

EXAMPLE 3

A catalyst was prepared in the same manner as for Catalyst A except that 1.54 g of yttrium nitrate hexahydrate was employed. The obtained catalyst was designated as Catalyst C. The theoretical supported amounts of Catalyst C were 20% by weight of nickel and 6% by weight of yttrium based on the total weight of the catalyst, on an assumption that both nickel and yttrium were reduced to the metallic states.

The reaction was conducted in the same manner as in Example 1 except that 1 g of Catalyst C was used as the catalyst. After the temperature rise, the reaction pressure reached 192 kg/cm$^2$ G. The results of the reaction are shown in Table 1.

EXAMPLE 4

9.91 g of nickel nitrate hexahydrate and 0.48 g of ytterbium nitrate trihydrate were dissolved in 28.5 ml of water, and 7.8 g of silica gel powder was added thereto. The mixture was left to stand at room temperature. One hour later, water was distilled off under reduced pressure, and the obtained powder was calcined at 120° C. for 16 hours. The dried powder was calcined under an air stream of 200 ml/min at 180° C. for one hour and further at 400° C. for one hour. After calcination, the powder was reduced with 30 ml/min of hydrogen in a nitrogen gas stream of 30 ml/min at 400° C. for two hours. At the time of calcination and reduction, the temperature raising rate was adjusted to 10° C./min. The obtained catalyst was designated as Catalyst D. The theoretical supported amounts of the Catalyst D were 20% by weight of nickel and 2% by weight of ytterbium based on the total weight of the catalyst, on an assumption that both nickel and ytterbium were reduced to the metallic states. As a result of measurement of X-ray diffraction of the catalyst, only a diffraction peak of nickel was ascertained, and the crystal size of nickel was 12.0 nm as obtained from the Scherrer's formula. Further, the specific surface area of this catalyst was measured by a BET method and was found to be 160 m$^2$/g.

The reaction was conducted in the same manner as in Example 1 except that 1.5 g of Catalyst D was used as the catalyst and 51.7 g of ammonia was employed. After the temperature rise, the reaction pressure reached 199 kg/cm$^2$ G. The results of the reaction are shown in Table 1.

EXAMPLE 5

A catalyst was prepared in the same manner as for Catalyst D except that 0.95 g of ytterbium nitrate trihydrate and 7.6 g of silica gel powder were used. The obtained catalyst was designated as Catalyst E. The theoretical supported amounts of Catalyst E were 20% by weight of nickel and 4% by weight of ytterbium based on the total weight of the catalyst, on an assumption that both nickel and ytterbium were reduced to the metallic states. As a result of measurement of X-ray diffraction of the catalyst, only a diffraction peak of nickel was ascertained, and the crystal size of nickel was 13.4 nm as obtained from the Scherrer's formula.

The reaction was conducted in the same manner as in Example 1 except that 1 g of catalyst E was used as the catalyst, and 51.7 g of ammonia was employed. After the temperature rise, the reaction pressure reached 198 kg/cm$^2$ G. The results of the reaction are shown in Table 1.

EXAMPLE 6

9.91 g of nickel nitrate hexahydrate and 0.59 g of samarium nitrate hexahydrate were dissolved in 28.5 ml of water, and 7.8 g of silica gel powder was added thereto. The mixture was left to stand at room temperature. One hour later, water was distilled off under reduced pressure, and the obtained powder was dried at 120° C. for 16 hours. The dried powder was calcined under an air stream of 200 ml/min at 180° C. for one hour and further at 400° C. for one hour. After calcination, the powder was reduced with 30 ml/min of hydrogen under a nitrogen gas stream of 30 ml/min at 400° C. for two hours. At the time of calcination and reduction, the temperature raising rate was adjusted to 10° C./min. The obtained catalyst was designated as Catalyst F. The theoretical supported amounts of Catalyst F were 20% by weight of nickel and 2% by weight of samarium based on the total weight of the catalyst, on an assumption that both nickel and samarium were reduced to the metallic states. As a result of measurement of X-ray diffraction of the catalyst, only a diffraction peak of nickel was ascertained, and the crystal size of nickel was 11.7 nm as obtained from the Scherrer's formula.

The reaction was conducted in the same manner as in Example 1 except that 1.5 g of Catalyst F was used as the catalyst and 51.7 g of ammonia was employed. After the temperature rise, the reaction pressure reached 200 kg/cm$^2$ G. The results of the reaction are shown in Table 1.

EXAMPLE 7

A catalyst was prepared in the same manner as for Catalyst F except that 1.18 g of samarium nitrate hexahydrate was used. The obtained catalyst was designated as Catalyst G. The theoretical supported amounts of Catalyst G were 20% by weight of nickel and 4% by weight of samarium based on the total amount of the catalyst, on an assumption that both nickel and samarium were reduced to the metallic states. As a result of measurement of X-ray diffraction of the catalyst, only a diffraction peak of nickel was ascertained, and the crystal size was 10.8 nm as obtained from the Scherrer's formula.

The reaction was conducted in the same manner as in Example 1 except that 1 g of Catalyst G was used as the catalyst and 51.7 g of ammonia was employed. After the temperature rise, the reaction pressure reached 197 kg/cm$^2$ G. The results of the reaction are shown in Table 1.

EXAMPLE 8

4.96 of nickel nitrate hexahydrate and 1.40 g of dysprosium nitrate hexahydrate were dissolved in 1 g of water, and 3.5 g of silica gel powder was immersed therein for one hour. Then, the powder was dried by an evaporator and then dried at 120° C. overnight. After drying, the powder was reduced with 30 ml/min of hydrogen under a stream of nitrogen-mixed gas of 30 ml/min at 500° C. for two hours. At the time of calcination and reduction, the temperature raising rate was adjusted to 10° C./min. The obtained catalyst was designated as Catalyst H. The amount of supported nickel of Catalyst H was 20% by weight, and the atomic ratio of Ni/Dy was 5.56.

The reaction was conducted in the same manner as in Example 1, except that 1.5 g of Catalyst H was used as the catalyst. The results of the reaction are shown in Table 1.

EXAMPLE 9

9.91 g of nickel nitrate hexahydrate and 0.45 g of lutetium nitrate dihydrate were dissolved in 28.5 g of water, and 7.8 g of silica gel powder was immersed therein for one hour. The powder was dried by an evaporator and dried at 120° C. overnight. Then, it was calcined under a dry air stream of 200 ml/min at 180° C. for one hour and further at 400° C. for one hour. After calcination, the powder was reduced with 30 ml/min of hydrogen under a stream of nitrogen-mixed gas of 30 ml/min at 500° C. for two hours. At the time of calcination and reduction, the temperature raising rate was adjusted to 10° C./min. The obtained catalyst was designated as Catalyst I. The amount of nickel supported on Catalyst I was 20% by weight, and the atomic ratio of Ni/Lu was 30.1.

The reaction was conducted in the same manner as in Example 1 except that 0.9 g of Catalyst I was used as the catalyst. The results of the reaction are shown in Table 1.

EXAMPLES 10 AND 11

The reaction was conducted in the same manner as in Example 1 except that Catalyst B was used in an amount of 0.8 g or 1.5 g as the catalyst. The results are shown in Table 1. The reaction pressure was 197 kg/cm$^2$ G when Catalyst B was used in an amount of 0.8 g and 196 kg/cm$^2$ G when it was used in an amount of 1.5 g.

COMPARATIVE EXAMPLE 1

A catalyst was prepared in the same manner as for Catalyst A except that no yttrium nitrate hexahydrate was employed. The obtained catalyst was designated as Comparative Catalyst A. The theoretical supported amount of Comparative Catalyst A was 20% by weight of nickel based on the total weight of the catalyst, on an assumption that nickel was reduced to the metallic state. Further, as a result of measurement of X-ray diffraction of the catalyst, only a diffraction peak of nickel was ascertained, and the crystal size of nickel was 13.0 nm as obtained from the Scherrer's formula.

The reaction was conducted in the same manner as in Example 1 except that 1.5 g of Comparative Catalyst A was used. After the temperature rise, the reaction pressure reached 197 kg/cm$^2$ G. The results of the reaction are shown in Table 1.

COMPARATIVE EXAMPLE 2

The reaction was conducted in the same manner as in Example 1 except that 2 g of Comparative Catalyst A was used. After the temperature rise, the reaction pressure reached 200 kg/cm$^2$ G. The results of the reaction are shown in Table 1.

EXAMPLE 12

The reaction was conducted in the same manner as in Example 2 except that 2.8 g of Catalyst B was used as the catalyst, the reaction temperature was changed to 170° C., and the reaction time was changed to 9 hours. After the temperature rise, the reaction pressure reached 145 kg/cm$^2$ G. The results of the reaction are shown in Table 2.

EXAMPLE 13

Into a 200 ml stainless steel autoclave equipped with an electromagnetic stirrer, 18 g of MEA, 75 g of ammonia, 3.6 g of water and 1.3 g of Catalyst A were charged, and hydrogen was introduced at room temperature so that the hydrogen partial pressure became 20 kg/cm$^2$. The temperature was raised to 185° C., and then the reaction was conducted for 6 hours at the same temperature. After the temperature rise, the reaction pressure reached 224 kg/cm$^2$ G. The results of the reaction are shown in Table 2.

EXAMPLE 14

The reaction was conducted in the same manner as in Example 1 except that 2.5 g of Catalyst D was used, and the reaction temperature was changed to 180° C. After the temperature rise, the reaction pressure reached 160 kg/cm² G. The results are shown in Table 2.

EXAMPLE 15

The reaction was conducted in the same manner as in Example 1 except that 1 g of Catalyst D was used, and hydrogen was introduced so that the hydrogen partial pressure became 10 kg/cm². After the temperature rise, the reaction pressure reached 184 kg/cm² G. The results are shown in Table 2.

EXAMPLE 16

The reaction was conducted in the same manner as in Example 1 except that 3.0 g of Catalyst F was used, and the reaction temperature was changed to 180° C. After the temperature rise, the reaction pressure reached 159 kg/cm² G. The results of the reaction are shown in Table 2.

EXAMPLE 17

A solution having 20.23 g of sodium hydroxide dissolved in 170 ml of water, was refluxed under heating, and a solution having 28.50 g of nickel nitrate hexahydrate, 5.22 g of yttrium nitrate and 33.86 g of aluminum nitrate dissolved in 120 ml of water, was dropwise added thereto over a period of 20 minutes. After completion of the dropwise addition, the mixture was refluxed under heating for further one hour. The obtained precipitate was washed with 3 l of water and dried at 120° C. for 16 hours. The dried powder was calcined under an air stream of 200 ml/min at 180° C. for one hour and further at 400° C. for one hour. After calcination, the powder was reduced with 30 ml/min of hydrogen under a nitrogen gas stream of 30 ml/min at 400° C. for two hours. At the time of calcination and reduction, the temperature raising rate was adjusted to 10° C./min. The obtained catalyst was designated as Catalyst J. The theoretical supported amounts of Catalyst J were 50% by weight of nickel and 10% by weight of yttrium based on the total weight of the catalyst, on an assumption that both nickel and yttrium were reduced to the metallic states.

The reaction was conducted in the same manner as in Example 1 except that 1.0 g of Catalyst J was employed. After the temperature rise, the reaction pressure reached 192 kg/cm² G. The results of the reaction are shown in Table 2.

EXAMPLE 18

4.96 g of nickel(II) nitrate hexahydrate and 0.28 g of dysprosium(III) nitrate hexahydrate were dissolved in 1 g of water, and 3.9 g of an activated alumina molded product (spherical, manufactured by Sumitomo Chemical Company Ltd.) was immersed therein for one hour. Then, the product was dried by an evaporator and then dried overnight at 120° C. Then, it was calcined under a dry air stream of 200 ml/min at 180° C. for one hour and further at 400° C. for one hour. After calcination, it was reduced with 30 ml/min of hydrogen under a nitrogen stream of 30 ml/min at 500° C. for two hours. At the time of calcination and reduction, the temperature raising rate was adjusted to 10° C./min. The obtained catalyst was designated as Catalyst K. The amount of Ni supported on this catalyst was 20% by weight, and the atomic ratio of Ni/Dy was 27.8.

Into a 200 ml stainless steel autoclave equipped with an electromagnetic stirrer, 30 g of MEA and 3 g of Catalyst K were charged, and the autoclave was flushed with nitrogen. Then, 50 g of ammonia was added, and hydrogen was introduced at room temperature so that the hydrogen partial pressure became 20 kg/cm². Then, the temperature was raised to 200° C. and maintained at this level for three hours. After completion of the reaction, the reaction solution was analyzed by gas chromatography. The results are shown in Table 3. As a result of the reaction, the value of EDA selectivity/(PIP selectivity+AEEA selectivity) was 2.51, which shows the ratio of the preferred product such as EDA to the undesirable products such as a cyclic product represented by PIP and a hydroxyl group-containing amine represented by AEEA.

EXAMPLE 19

4.96 g of nickel(II) nitrate hexahydrate and 0.29 g of gadolinium(III) nitrate hexahydrate were dissolved in 1 g of water, and 3.9 g of an activated alumina molded product (spherical, manufactured by Sumitomo Chemical Company Ltd.) was immersed therein for one hour. The product was dried by an evaporator and then dried overnight at 120° C. Then, it was calcined in a dry air stream of 200 ml/min at 180° C. for one hour and further at 400° C. for one hour. After calcination, it was reduced with 30 ml/min of hydrogen under a nitrogen stream of 30 ml/min at 500° C. for two hours. At the time of calcination and reduction, the temperature raising rate was adjusted to 10° C./min. The obtained catalyst was designated as Catalyst L. The amount of nickel supported on this catalyst was 20% by weight, and the atomic ratio of Ni/Gd was 26.5.

The reaction was conducted in the same manner as in Example 18 except that 3 g of Catalyst L was employed. The results are shown in Table 3. Further, as a result of the reaction, the value of EDA selectivity/(PIP selectivity +AEEA selectivity) was 2.46, which shows the ratio of the desired product such as EDA to the undesirable products such as a cyclic product represented by PIP and a hydroxyl group-containing amine represented by AEEA.

COMPARATIVE EXAMPLE 3

A Comparative Catalyst was prepared in the same manner as for Catalyst K except that no dysprosium was added. The method for the preparation will be described in detail. 4.96 g of nickel(II) nitrate hexahydrate was dissolved in 1 g of water, and 4.0 g of an activated alumina molded product (spherical, manufactured by Sumitomo Chemical Company Ltd.) was immersed therein for one hour. The product was dried by an evaporator and then dried overnight at 120° C. The dried product was calcined in a dry air stream of 200 ml/min at 180° C. for one hour and further at 400° C. for one hour. After calcination, it was reduced with 30 ml/min of hydrogen under a nitrogen stream of 30 ml/min at 500° C. for two hours. At the time of calcination and reduction, the temperature raising rate was adjusted to 10° C/min. The obtained catalyst was designated as Comparative Catalyst B. The amount of nickel supported on this catalyst was 20% by weight.

The reaction was conducted in the same manner as in Example 18 except that Comparative Catalyst B was used instead of Catalyst K. The results are shown in Table 3. Further, as a result of the reaction, the value of EDA selectivity/(PIP selectivity +AEEA selectivity) was 2.34, which shows the ratio of the preferred product such as EDA to the undesirable products such as a cyclic product represented by PIP and a hydroxyl group-containing amine represented by AEEA.

EXAMPLE 20 TO 27

Catalysts M to T were prepared in the same manner as in Example 18 except that a nitrate of M as identified in Table 4 was used instead of dysprosium nitrate hexahydrate. The amount of the nitrate of M was adjusted so that it became 2% by weight based on the total weight of the catalyst, on the assumption that M was reduced to the metallic state.

The reaction was conducted in the same manner as in Example 18 except that 3 g of this catalyst was employed. The results are shown in Table 4.

EXAMPLE 28

4.96 g of nickel(II) nitrate hexahydrate and 0.50 g of gadolinium(III) nitrate hexahydrate were dissolved in 1 g of water, and 3.8 g of silica-calcia powder (manufactured by Nikki Kagaku K.K.) was immersed therein for one hour. The powder was dried by an evaporator and then dried overnight at 120° C. After drying, it was reduced with 30 ml/min of hydrogen under a nitrogen stream of 30 ml/min at 400° C. for two hours. The temperature raising rate was adjusted to 10° C./min. The obtained catalyst was designated as Catalyst U. The amount of Ni supported on this catalyst was 20% by weight, and the atomic ratio of Ni/Gd was 15.4.

The reaction was conducted in the same manner as in Example 18 except that 1.5 g of Catalyst U was used as the catalyst. The results are shown in Table 5. Further, as a result of the reaction, the value of EDA selectivity/(PIP selectivity +AEEA selectivity) was 2.67, which represents a ratio of the desired product such as EDA to the undesired products such as a cyclic product represented by PIP and a hydroxyl group-containing amine represented by AEEA.

EXAMPLE 29

4.96 g of nickel(II) nitrate hexahydrate was dissolved in 1 g of water, and 4.0 g of dysprosium oxide powder was added thereto. The powder was dried by an evaporator and then dried overnight at 120° C. Then, it was calcined under a dry air stream at 180° C. for one hour and further at 400° C. for one hour. After calcination, it was reduced under a 50% hydrogen/nitrogen stream at 400° C. for two hours. The obtained catalyst was designated as Catalyst V. The amount of Ni supported on Catalyst V was 20% by weight, and the atomic ratio of Ni/Dy was 0.80.

The reaction was conducted in the same manner as in Example 18 except that 1.5 g of Catalyst V was used as the catalyst. The results are shown in Table 5.

EXAMPLE 30

Into a 200 ml stainless steel autoclave equipped with an electromagnetic stirrer, 18 g of MEA and 2 g of Catalyst H were charged, and the autoclave was flushed with nitrogen. Then, 50 g of ammonia was added thereto, and hydrogen was introduced at room temperature so that the hydrogen partial pressure became 20 kg/cm$^2$. Then, the temperature was raised to 170° C. and maintained at that level for 9 hours. After completion of the reaction, the reaction solution was analyzed by gas chromatography. The results are shown in Table 5.

EXAMPLE 31

Into a 200 ml stainless steel autoclave equipped with an electromagnetic stirrer, 30 g of MEA and 1.5 g of Catalyst U were charged, and the autoclave was flushed with nitrogen. Then, 50 g of ammonia was added thereto, and hydrogen was introduced at room temperature so that the hydrogen partial pressure became 20 kg/cm$^2$. Then, the temperature was raised to 180° C. and maintained at that level for 7 hours. After completion of the reaction, the reaction solution was analyzed by gas chromatography. The results are shown in Table 5.

EXAMPLE 32

9.91 g of nickel nitrate hexahydrate and 0.91 g of lutetium nitrate dihydrate was dissolved in 28.5 g of water, and 7.6 g of alumina powder was immersed therein for one hour. The powder was dried by an evaporator and dried overnight at 120° C. After drying, it was reduced with 30 ml/min of hydrogen under a nitrogen stream of 30 ml/min at 400° C. for two hours. The temperature raising rate was adjusted to 10° C./min. The obtained catalyst was designated as Catalyst W. The amount of Ni supported on the catalyst was 20% by weight, and the atomic ratio of Ni/Lu was 14.9.

Into a 200 ml stainless steel autoclave equipped with an electromagnetic stirrer, 18 g of MEA and 1.5 g of Catalyst W were charged, and the autoclave was flushed with nitrogen. Then, 50 g of ammonia was added thereto, and hydrogen was introduced so that the hydrogen partial pressure at room temperature became 20 kg/cm$^2$. Then, the temperature was raised to 200° C. and maintained at that level for 3 hours. After completion of the reaction, the reaction solution was analyzed by gas chromatography. The results are shown in Table 5.

EXAMPLE 33

Into a 200 ml stainless steel autoclave equipped with an electromagnetic stirrer, 18 g of MEA and 1.5 g of Catalyst W were charged, and the autoclave was flushed with nitrogen. Then, 50 g of ammonia was added thereto, and hydrogen was introduced so that the hydrogen partial pressure at room temperature became 20 kg/cm$^2$. Then, the temperature was raised to 180° C. and maintained at that level for 3 hours. After completion of the reaction, the reaction solution was analyzed by gas chromatography. The results are shown in Table 5.

EXAMPLE 34

50 g of nickel sulfate hexahydrate and 3.6 g of dysprosium sulfate octahydrate were dissolved in 200 g of water, and 6 g of diatomaceous earth powder (manufactured by Johns-Manville Company) was added thereto, and the mixture was maintained at 70° C. under stirring. Then, a solution having 40 g of soda ash dissolved under heating in 150 g of water, was dropwise added thereto over a period of 30 minutes, and then the mixture was aged for one hour. Then, the mixture was cooled to room temperature, and the precipitate was collected by filtration and washed with water, it was dried overnight at 120° C. and then calcined in a dry air stream at 300° C. for two hours. It was then reduced under a 50% hydrogen/nitrogen gas stream at 330° C. for two hours.

The obtained catalyst was designated as Catalyst X. The amount of Ni supported on Catalyst X was 59% by weight, and the atomic ratio of Ni/Dy was 20.

Into a 200 ml stainless steel autoclave equipped with an electromagnetic stirrer, 60 g of EDA, 30 g of MEA and 1 g of Catalyst X were charged, and the autoclave was flushed with nitrogen. Then, hydrogen was introduced so that the hydrogen partial pressure at room temperature became 20 kg/cm$^2$. The temperature was raised to 200° C. and maintained at that level for 3 hours. After cooling, the reaction solution was analyzed by gas chromatography. As a result, the MEA conversion was 18.7%, and the composition of the products excluding starting materials and formed water, was as follows: 18.3% by weight of PIP, 58.1% by weight of DETA, 7.1% by weight of AEEA, 1.9% by weight of AEP and 5.0% by weight of TETA.

EXAMPLE 35

50 g of nickel sulfate hexahydrate and 3.6 g of gadolinium sulfate octahydrate were dissolved in 200 g of water, and 6 g of diatomaceous earth powder (manufactured by Johns-Manville Company) was added thereto. The mixture was maintained at 70° C. under stirring. A solution having 40 g of soda ash dissolved under heating in 150 g of water, was dropwise added thereto over a period of 30 minutes, and the mixture was aged for one hour. Then, the mixture was cooled to room temperature, and the precipitate was collected by filtration and washed with water. It was then dried overnight at 120° C. and calcined in a dry air stream at 300° C. for two hours. It was then reduced under a 50% hydrogen/nitrogen gas stream at 330° C. for two hours. The obtained catalyst was designated as Catalyst Y. The amount of Ni supported on Catalyst Y was 62% by weight, and the atomic ratio of Ni/Gd was 39.

The reaction was conducted in the same manner as in Example 23 except that 1 g of Catalyst Y was used as the catalyst. The reaction solution was analyzed by gas chromatography. As a result, the MEA conversion was 18.7%, and the composition of the products excluding starting materials and formed water was as follows: 18.3% by weight of PIP, 58.1% by weight of DETA, 7.1% by weight of AEEA, 1.9% by weight of AEP and 5.0% by weight of TETA.

EXAMPLE 36

17.9 g of nickel sulfate hexahydrate and 0.89 g of lutetium chloride hexahydrate were dissolved in 28.5 g of water. Then, 5.6 g of diatomaceous earth powder was added thereto and immersed for one hour. It was dried by an evaporator and then dried overnight at 120° C. Then, it was calcined under a dry air stream of 200 ml/min at 180° C. for one hour and further at 400° C. for one hour. After calcination, it was reduced with 30 ml/min of hydrogen under a nitrogen stream of 30 ml/min, at 400° C. for two hours. The temperature raising rate was adjusted to 10° C./min. The obtained catalyst was designated as Catalyst Z. The amount of nickel supported on this catalyst was 40% by weight, and the atomic ratio of Ni/Lu was 14.9.

The reaction was conducted in the same manner as in Example 23 except that 1 g of Catalyst Z was used as the Catalyst. As a result, the MEA conversion was 15.2%, and the composition of products excluding starting materials and formed water was as follows: 17.5% by weight of PIP, 61.5% by weight of DETA, 8.5% by weight of AEEA, 1.2% by weight of AEP and 4.5% by weight of TETA.

TABLE 1

|  | Catalyst | Amount of catalyst (g) | MEA conversion (%) | \multicolumn{7}{c}{Selectivities for reaction products (mol %)} |||||||
|---|---|---|---|---|---|---|---|---|---|---|
|  |  |  |  | EDA | PIP | DETA | AEEA | AEP | HEP | TETA |
| Example 1 | Catalyst A | 1.0 | 43.3 | 57.3 | 7.9 | 10.1 | 8.5 | 1.3 | 0.6 | 0.0 |
| Example 2 | Catalyst B | 1.0 | 42.9 | 58.6 | 7.3 | 8.5 | 7.5 | 0.9 | 0.4 | 0.0 |
| Example 3 | Catalyst C | 1.0 | 35.8 | 56.2 | 6.5 | 8.2 | 9.7 | 0.9 | 0.7 | 0.0 |
| Example 4 | Catalyst D | 1.5 | 64.2 | 53.0 | 15.0 | 10.3 | 7.0 | 2.9 | 1.0 | 0.1 |
| Example 5 | Catalyst E | 1.0 | 43.3 | 66.3 | 8.1 | 7.9 | 10.2 | 1.2 | 0.7 | 0.9 |
| Example 6 | Catalyst F | 1.5 | 63.8 | 51.5 | 14.7 | 9.9 | 7.3 | 2.9 | 0.9 | 0.4 |
| Example 7 | Catalyst G | 1.0 | 51.2 | 61.1 | 10.5 | 9.3 | 9.5 | 1.8 | 0.8 | 1.6 |
| Example 8 | Catalyst H | 1.5 | 41.8 | 64.3 | 7.0 | 8.2 | 13.0 | 1.1 | 0.5 | 1.1 |
| Example 9 | Catalyst I | 0.9 | 37.2 | 59.1 | 6.9 | 4.9 | 9.8 | 0.9 | 0.8 | 0.5 |
| Example 10 | Catalyst B | 0.8 | 38.8 | 59.3 | 5.3 | 7.8 | 3.9 | 0.6 | 0.3 | 0.0 |
| Example 11 | Catalyst B | 1.5 | 57.3 | 58.1 | 13.0 | 11.3 | 6.2 | 2.1 | 1.0 | 0.0 |
| Comparative Example 1 | Comparative Catalyst A | 1.5 | 33.0 | 56.8 | 7.2 | 4.7 | 11.5 | 1.0 | 1.0 | 0.3 |
| Comparative Example 2 | Comparative Catalyst A | 2.0 | 54.6 | 53.3 | 13.1 | 7.1 | 10.0 | 2.1 | 1.1 | 0.7 |

TABLE 2

|  | Catalyst | MEA conversion (%) | \multicolumn{7}{c}{Selectivities for reaction products (mol %)} |||||||
|---|---|---|---|---|---|---|---|---|---|
|  |  |  | EDA | PIP | DETA | AEEA | AEP | HEP | TETA |
| Example 12 | Catalyst B | 62.7 | 59.2 | 10.0 | 14.2 | 6.2 | 1.1 | 0.2 | 0.0 |
| Example 13 | Catalyst A | 24.1 | 81.7 | 2.5 | 0.0 | 0.0 | 0.0 | 0.0 | 0.0 |
| Example 14 | Catalyst D | 29.6 | 62.7 | 4.8 | 5.0 | 13.3 | 0.5 | 0.4 | 0.5 |
| Example 15 | Catalyst D | 30.1 | 53.4 | 8.4 | 5.6 | 20.3 | 1.4 | 2.4 | 1.3 |
| Example 16 | Catalyst F | 33.8 | 65.3 | 6.0 | 6.4 | 11.8 | 1.0 | 0.5 | 0.5 |
| Example 17 | Catalyst J | 39.2 | 47.1 | 5.1 | 5.9 | 18.8 | 0.3 | 0.9 | 1.4 |

TABLE 3

| | Catalyst | MEA conversion (%) | Selectivities for reaction products (mol %) | | | | | | |
|---|---|---|---|---|---|---|---|---|---|
| | | | EDA | PIP | DETA | AEEA | AEP | TETA | TEPA |
| Example 18 | Catalyst K | 61.9 | 50.3 | 12.1 | 13.8 | 8.0 | 1.2 | 3.6 | 1.7 |
| Example 19 | Catalyst L | 63.6 | 52.0 | 13.3 | 15.5 | 7.9 | 1.4 | 2.4 | 1.0 |
| Comparative Example 3 | Comparative Catalyst B | 53.9 | 55.3 | 10.6 | 12.2 | 13.0 | 1.0 | 2.8 | 1.4 |

TABLE 4

| | Catalyst | M | Ni/M atomic ratio | MEA conversion (%) | Selectivities for reaction products (mol %) | | | | | |
|---|---|---|---|---|---|---|---|---|---|---|
| | | | | | EDA | PIP | DETA | AEEA | AEP | TETA |
| Example 20 | Catalyst M | Sc | 7.7 | 58.5 | 54.1 | 9.5 | 11.4 | 9.6 | 0.9 | 2.8 |
| Example 21 | Catalyst N | Pr | 24.0 | 59.0 | 53.4 | 9.9 | 11.9 | 9.7 | 1.0 | 2.9 |
| Example 22 | Catalyst O | Nd | 24.6 | 59.9 | 53.0 | 11.3 | 13.8 | 8.4 | 1.1 | 3.4 |
| Example 23 | Catalyst P | Eu | 25.9 | 63.2 | 52.2 | 12.3 | 14.2 | 6.5 | 0.9 | 3.5 |
| Example 24 | Catalyst Q | Tb | 27.1 | 62.1 | 51.9 | 11.8 | 13.6 | 8.1 | 0.8 | 3.3 |
| Example 25 | Catalyst R | Ho | 28.1 | 57.6 | 53.3 | 9.9 | 12.9 | 8.1 | 0.9 | 2.3 |
| Example 26 | Catalyst S | Er | 28.5 | 56.7 | 55.6 | 8.4 | 11.2 | 10.2 | 1.1 | 2.1 |
| Example 27 | Catalyst T | Tm | 28.8 | 63.2 | 51.7 | 12.4 | 14.0 | 7.5 | 1.2 | 2.9 |

TABLE 5

| | Catalyst | MEA conversion (%) | Selectivities for reaction products (mol %) | | | | |
|---|---|---|---|---|---|---|---|
| | | | EDA | PIP | DETA | AEEA | TETA |
| Example 28 | Catalyst U | 51.3 | 58.4 | 7.0 | 10.4 | 14.8 | 1.7 |
| Example 29 | Catalyst V | 63.0 | 45.3 | 14.9 | 13.1 | 8.8 | 3.7 |
| Example 30 | Catalyst H | 42.9 | 59.6 | 6.3 | 10.8 | 8.2 | 0.6 |
| Example 31 | Catalyst U | 24.7 | 70.1 | 5.1 | 8.1 | 11.4 | 1.0 |
| Example 32 | Catalyst W | 50.3 | 55.7 | 10.8 | 5.9 | 8.6 | 0.2 |
| Example 33 | Catalyst W | 28.9 | 61.9 | 4.5 | 5.3 | 12.1 | 0.3 |

What is claimed is:

1. A process for producing an ethylenamine, which comprises reacting ammonia and/or an ethylenamine with an ethanolamine in a liquid phase in the presence of hydrogen to obtain an ethylenamine having an increased number of ethylene chains over the ammonia and/or the ethylenamine used as starting material, wherein a catalyst comprising Ni and M elements wherein Ni is in the form of nickel metal or nickel oxide and M is in the form of metal or an oxide of at least one element selected from the group consisting of scandium, yttrium, phraseodymium, neodymium, samarium, europium, gadolinium, terbium, dysprosium, holmium, erbium, thulium, ytterbium and lutetium, is used for the reaction.

2. The process according to claim 1, wherein M is yttrium, samarium or ytterbium, and the atomic ratio of Ni/M is from 1 to 80.

3. The process according to claim 1, wherein M is scandium, praseodymium, neodymium, europium, gadolinium, terbium, dysprosium, holmium, erbium, thulium or luthetium, and the atomic ratio of Ni/M is from 0.01 to 100.

4. The process according to claim 1, wherein the ethanolamine is monoethanolamine, diethanolamine, triethanolamine, N-(2-aminoethyl)ethanolamine or N-(2-hydroxyethyl)piperazine.

5. The process according to claim 1, wherein the ethylenamine used as the starting material is ethylenediamine, diethylenetriamine, triethylenetetramine, tetraethylenepentamine, pentaethylenehexamine, piperazine, N-(2-aminoethyl)piperazine or triethylenediamine.

6. The process according to claim 1, wherein the reaction of ammonia with an ethanolamine is conducted at a molar ratio of the ammonia/the ethanolamine of from 1 to 50.

7. The process according to claim 1, wherein the reaction of an ethylenamine with an ethanolamine is conducted at a molar ratio of the ethylenamine/the ethanolamine of from 0.1 to 20.

8. The process according to claim 1, wherein the hydrogen is supplied at a molar ratio of the hydrogen/the ethanolamine of from 0.01 to 5.

9. The process according to claim 1, wherein the reaction is conducted at a temperature of from 110° to 290° C.

10. The process according to claim 1, wherein the reaction is conducted in a liquid phase.

* * * * *